(12) United States Patent
Vaquero

(10) Patent No.: US 7,947,049 B2
(45) Date of Patent: May 24, 2011

(54) IOL INJECTOR

(75) Inventor: Edward Vaquero, Fairport, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 740 days.

(21) Appl. No.: 10/813,863

(22) Filed: Mar. 31, 2004

(65) Prior Publication Data

US 2005/0222578 A1 Oct. 6, 2005

(51) Int. Cl.
*A61F 2/16* (2006.01)
*A61F 9/00* (2006.01)

(52) U.S. Cl. ........................................... 606/107

(58) Field of Classification Search .................. 606/107, 606/99, 17.6, 187, 86 A; 623/6.12, 17.16; 604/57, 59, 60, 15; 221/240, 156–173
See application file for complete search history.

(56) References Cited

U.S. PATENT DOCUMENTS

| | | | | |
|---|---|---|---|---|
| 3,386,438 A * | 6/1968 | Stevens | ......................... | 604/272 |
| 4,934,363 A * | 6/1990 | Smith et al. | .................. | 606/107 |
| 5,772,667 A | 6/1998 | Blake | | |
| 5,800,442 A * | 9/1998 | Wolf et al. | .................... | 606/107 |
| 5,935,096 A * | 8/1999 | Barrett | ............................ | 604/22 |
| 6,139,539 A * | 10/2000 | Baudino | ........................ | 604/537 |
| 6,471,708 B2 * | 10/2002 | Green | ............................ | 606/107 |
| 6,491,697 B1 * | 12/2002 | Clark et al. | .................... | 606/107 |
| 2002/0022881 A1 * | 2/2002 | Figueroa et al. | ............ | 623/6.12 |
| 2003/0233078 A1 * | 12/2003 | Swick | ............................ | 604/279 |
| 2005/0033308 A1 * | 2/2005 | Callahan et al. | ............. | 606/107 |
| 2009/0281620 A1 * | 11/2009 | Sacharoff et al. | ........... | 623/6.22 |

FOREIGN PATENT DOCUMENTS

| | | |
|---|---|---|
| EP | 0270257 A1 | 6/1988 |
| WO | WO 03/077805 A1 | 9/2003 |
| WO | WO 2004/010903 A1 | 2/2004 |

* cited by examiner

*Primary Examiner* — Todd E Manahan
*Assistant Examiner* — Amy Lang
(74) *Attorney, Agent, or Firm* — Jeffrey B Powers

(57) ABSTRACT

A device for injecting an intraocular lens (IOL) into an eye, the device having an injector body including a lumen and an open tip wherethrough the IOL is expressed from the device. An IOL loading bay is located in the passageway wherein the IOL is positioned and compressed. In a first aspect of the invention, the passageway diameter increases from a point adjacent the loading bay to the open tip to reduce compressive force on the IOL as it travels through the lumen. In another aspect of the invention, the plunger tip has a shape and diameter which has a close, sliding fit with the shape and diameter of the passageway to reduce the chance of the IOL becoming wedged between the plunger tip and the passageway wall as the plunger tip engages and advances the IOL through the passageway.

13 Claims, 7 Drawing Sheets

IOL INJECTOR

BACKGROUND OF THE INVENTION

The present invention relates to ophthalmic surgical devices and methods. More particularly, the present invention relates to a device and method for inserting an intraocular lens (IOL) into an eye.

IOLs are artificial lenses used to replace the natural crystalline lens of the eye when the natural lens has cataracts or is otherwise diseased. IOLs are also sometimes implanted into an eye to correct refractive errors of the eye in which case the natural lens may remain in the eye together with the implanted IOL. The IOL may be placed in either the posterior chamber or anterior chamber of the eye. IOLs come in a variety of configurations and materials. Some common IOL styles include the so-called open-looped haptics which include the three-piece type having an optic and two haptics attached to and extending from the optic; the one-piece type wherein the optic and haptics are integrally formed (e.g., by machining the optic and haptics together from a single block of material); and also the closed looped haptic IOLs. Yet a further style of IOL is called the plate haptic type wherein the haptics are configured as a flat plate extending from opposite sides of the optic. The IOL may be made from a variety of materials or combination of materials such as PMMA, silicone, hydrogels and silicone hydrogels, etc.

Various instruments and methods for implanting the IOL in the eye are known. In one method, the surgeon simply uses surgical forceps having opposing blades which are used to grasp the IOL and insert it through the incision into the eye. While this method is still practiced today, more and more surgeons are using more sophisticated IOL inserter devices which offer advantages such as affording the surgeon more control when inserting the IOL into the eye. IOL inserter devices have recently been developed with reduced diameter insertion tips which allow for a much smaller incision to be made in the cornea than is possible using forceps alone. Smaller incision sizes (e.g., less than about 3 mm) are preferred over larger incisions (e.g., about 3.2 to 5+ mm) since smaller incisions have been attributed to reduced post-surgical healing time and complications such as induced astigmatism.

Since IOLs are very small and delicate articles of manufacture, great care must be taken in their handling. In order for the IOL to fit through the smaller incisions, they need to be folded and/or compressed prior to entering the eye wherein they will assume their original unfolded/uncompressed shape. The IOL inserter device must therefore be designed in such a way as to permit the easy passage of the IOL through the device and into the eye, yet at the same time not damage the delicate IOL in any way. Should the IOL be damaged during delivery into the eye, the surgeon will most likely need to extract the damaged IOL from the eye and replace it with a new IOL, a highly undesirable surgical outcome.

Thus, as explained above, the IOL inserter device must be designed to permit easy passage of the IOL therethrough. It is equally important that the IOL be expelled from the tip of the IOL inserter device and into the eye in a predictable orientation and manner. Should the IOL be expelled from the tip too quickly or in the wrong orientation, the surgeon must further manipulate the IOL in the eye which could result in trauma to the surrounding tissues of the eye. It is therefore highly desirable to have an inserter device which allows for precise loading of the IOL into the inserter device and which will pass and expel the IOL from the inserter device tip and into the eye in a controlled, predictable and repeatable manner.

To ensure controlled expression of the IOL through the tip of the IOL inserter device, the IOL must first be loaded into the IOL inserter device. The loading of the IOL into the inserter device is therefore a precise and very important step in the process. Incorrect loading of an IOL into the inserter device is oftentimes cited as the reason for a failed IOL delivery sequence. Many IOL injector devices on the market today require the IOL to be loaded into the injector at the time of surgery by the attending nurse and/or surgeon. Due to the delicate nature of the IOL, there is a risk that the nurse and/or surgeon will inadvertently damage the IOL and/or incorrectly load the IOL into the injector device resulting in a failed implantation. Direct handling and/or loading of the IOL into the injector by the nurse and/or surgeon is therefore undesirable.

In a typical IOL inserter device, the IOL inserter utilizes a plunger having a tip which engages the IOL (which has been previously loaded and compressed into the inserter lumen) to pass it through the inserter lumen. The IOL thus interfaces with the plunger tip as well as the lumen of the inserter device. The lumen typically is dimensioned with a narrowing toward the open tip thereof in order to further compress the IOL as it is advanced through the lumen. The tip of the lumen is sized for insertion through the surgical incision which, as stated above, is presently preferred in the sub 3 mm range. Thus, an inserter lumen will typically be dimensioned larger at the load area of the IOL and gradually decrease in diameter to the tip of the lumen where the IOL is expressed into the eye. It will be appreciated that the compressed diameter of the IOL at the lumen tip is the same as the inner diameter of the lumen tip, preferably sub 3 mm as stated above. Each of these component interfaces are dynamic in the sense that the forces acting between the interfacing components (i.e., the IOL, the plunger tip and the inserter lumen) will vary as the IOL is pushed through the lumen. Control of these dynamic forces is therefore of utmost importance or otherwise the IOL may be damaged during delivery due to excessive compressive forces acting thereon. For example, as the IOL is advanced by the plunger through an ever-decreasing diameter lumen, the IOL is being compressed while at the same time the forces necessary to push the IOL through the lumen increase. This may lead to excessive force between the plunger tip and the IOL resulting in possible damage to the IOL and/or uncontrolled release of the IOL from the lumen tip. Also, the force of the plunger tip may cause the IOL to twist and/or turn as it is moved through the inserter whereby the force between the IOL and the plunger tip and/or the inserter lumen may uncontrollably increase to the point of IOL damage.

Various inserter devices have been proposed which attempt to address these problems, yet there remains a need for an IOL inserter and method which reduces the likelihood of IOL damage during delivery through the injector device.

SUMMARY OF THE INVENTION

The injector comprises a device body having a longitudinal passageway (lumen) defined by an inner passageway wall terminating at an open tip. A plunger having a longitudinal plunger shaft and a plunger tip telescopes with the lumen of the device body. A loading bay is located in the lumen wherein an IOL is positioned and compressed. In a first aspect of the invention, the lumen increases in diameter from a point adjacent the loading bay to the open tip. This allows the IOL to gradually expand as it is advanced through the passageway by the plunger tip. This reduces forces on the IOL and thus reduces the chance of IOL damage caused by excessive forces exerted thereon during IOL delivery through and out the device. At the same time, the outer diameter of the device body along the same length remains constant at the desired diameter (e.g., sub 3 mm) so that the eye incision size need not be increased even though the inner diameter of the passageway is increasing. It will be appreciated that a compressed IOL will naturally seek a position of less compressive force. Thus, once the IOL is initially advanced by the plunger, the increasing diameter of the passageway adjacent the loading bay urges the IOL to continue to move in that direction (i.e., toward the open tip). The amount of force required to advance the IOL therethrough is thereby reduced and the goal of less force on the IOL during delivery through the inserter device is realized.

In another aspect of the invention, the cross-sectional shape of the plunger tip is substantially the same as the cross-sectional shape and slightly smaller than the diameter of the inner wall defining the lumen along the length where the IOL travels. As such, the plunger tip is in close, sliding relation to the passageway. This reduces the likelihood that the IOL can become wedged between the plunger tip and the passageway wall, a problem of prior injector designs having relatively large spacing between the plunger tip and inner lumen wall.

The injector includes means for compressing, rolling or otherwise forcing the IOL into a smaller cross-section for delivery through the injector. In a preferred embodiment of the invention, the injector device includes a compressor which extends laterally of the IOL loading bay of the injector body. The compressor is movable between fully open and fully closed positions and is initially in the open position. Once the IOL is positioned in the loading bay of the passageway, the compressor is moved to the closed position which compresses the IOL. The plunger is advanced at the proximal end of the injector device causing the tip of the plunger to engage the proximal end of the compressed IOL. As the plunger is advanced further, the IOL is pushed through the open distal tip of the injector body and expressed into the eye in the intended manner.

DETAILED DESCRIPTION

Figure 1:
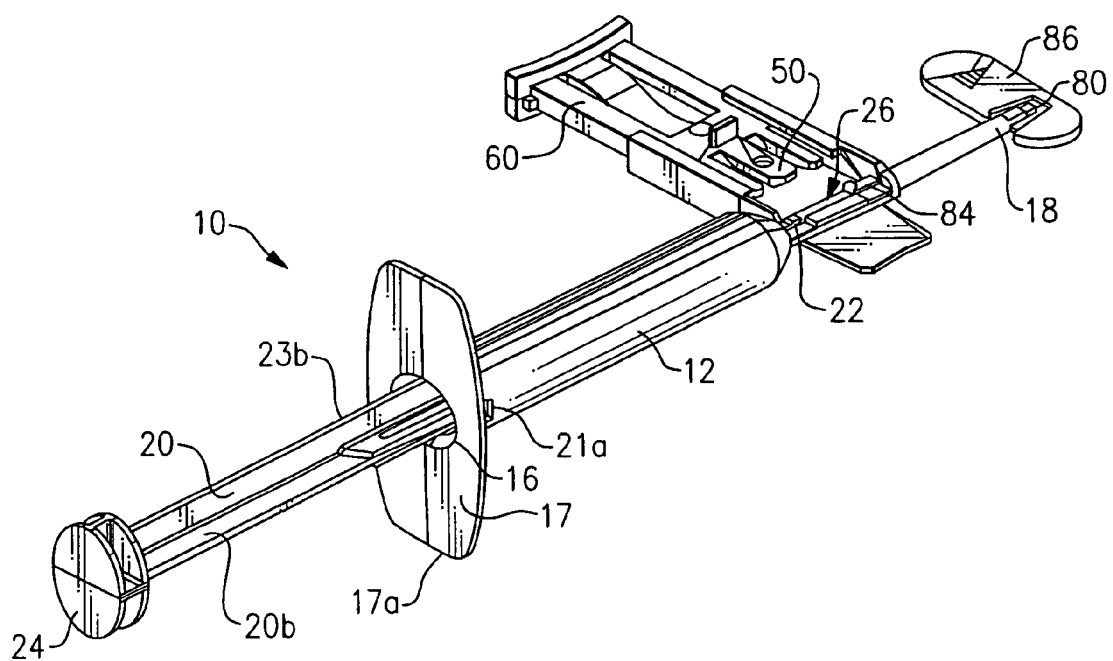
FIG. 1 is a perspective view of an IOL injector according to one embodiment of the invention.

Referring to the Figures, a representative IOL injector device is indicated generally by the reference numeral 10. The injector device 10 includes an injector body 12 having a longitudinal lumen 14 extending from the proximal end 16 to distal end 18 thereof. The lumen may assume any desired cross-sectional shape although circular or oval shapes are preferred. Proximal end 16 may include a finger hold flange 17 preferably configured with a straight edge 17a as shown for resting device 10 on a flat surface. A plunger 20, having distal and proximal lengths 20a, 20b, respectively, and a distal plunger tip 22 (see FIG. 2A) and proximal thumb press 24, telescopes within lumen 14 for engaging and pushing the IOL 30 through lumen 14 and out of distal tip 18a. The IOL delivery sequence will be explained in more detail below. It is understood that the overall configuration of the injector body 12 may vary from that shown and described herein. It is furthermore understood that the components of the injector device 10 may be made of any suitable material (e.g., polypropylene) and may be wholly or partly opaque, transparent or translucent to better visualize the IOL within the injector device and the IOL delivery sequence.

Injector body 12 further includes an opening 26 which opens into lumen 14. Opening or "IOL loading bay" 26 accepts an IOL 30 therein for delivery of the IOL out distal tip 18a. In one possible embodiment, device 10 includes an IOL retainer 40 (FIGS. 3A-E) used for loading the IOL 30 into loading bay 26. Retainer 40 will be described herein in relation to injector device 10 for purposes of description, it being understood other IOL loading methods may be employed (including simply placing IOL 30 in loading bay 26 with a pair of forceps, for example). The retainer 40 and another embodiment of an IOL retainer are seen in commonly owned co-pending application Ser. Nos. 10/651,785 and 10/813,862, both of which are incorporated by reference herein. As explained in more detail in these copending applications, retainer 40 and IOL 30 may be coupled and packaged together or coupled to and packaged with an injector device 12 such that the surgeon or nurse need not handle and/or manipulate the IOL directly when loading the IOL 30 into the device 10.

Figure 3A:
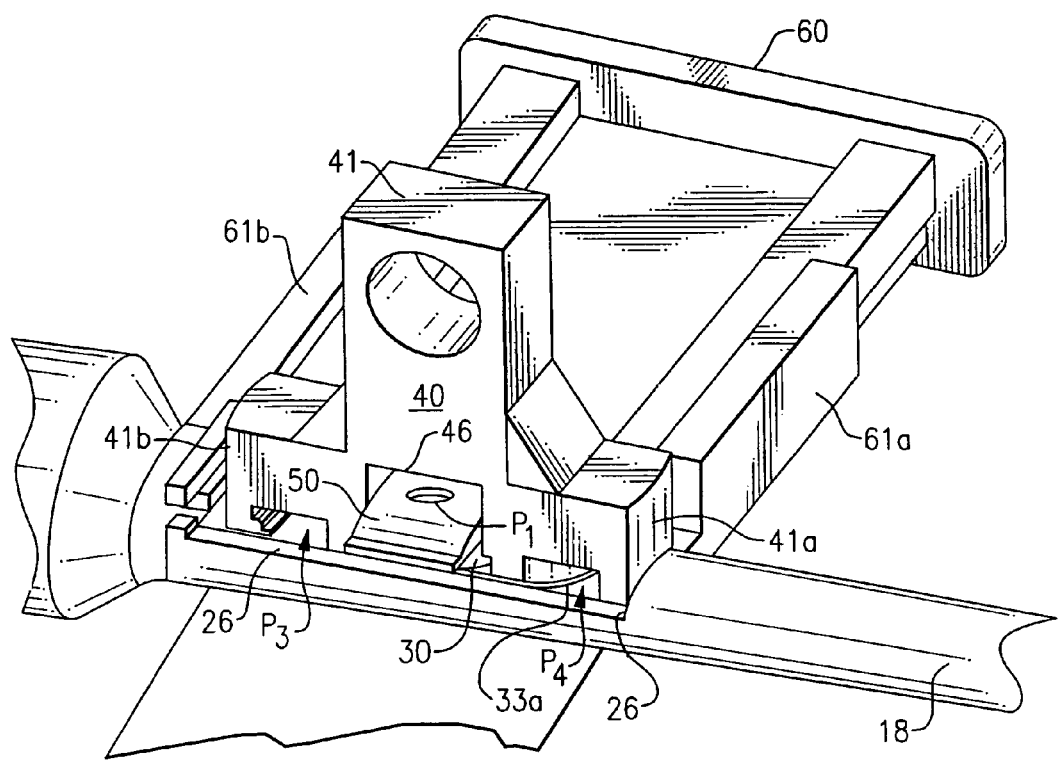
FIG. 3A is an enlarged perspective view of the loading bay area of the injector device of FIG. 1.
Figure 3B:
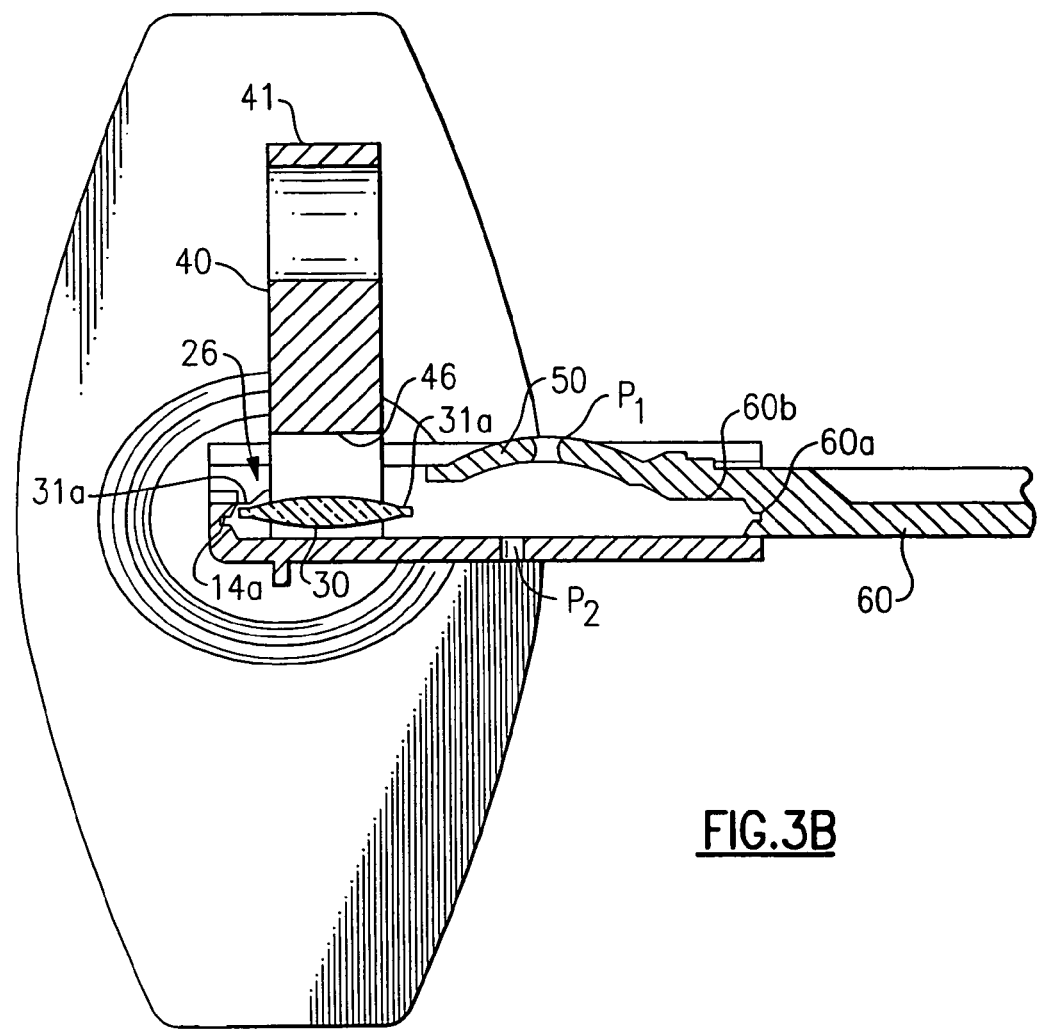
FIG. 3B is a cross-sectional view taken through the IOL loading bay of the injector device with the compressor drawer in the fully open position.
Figure 3C:
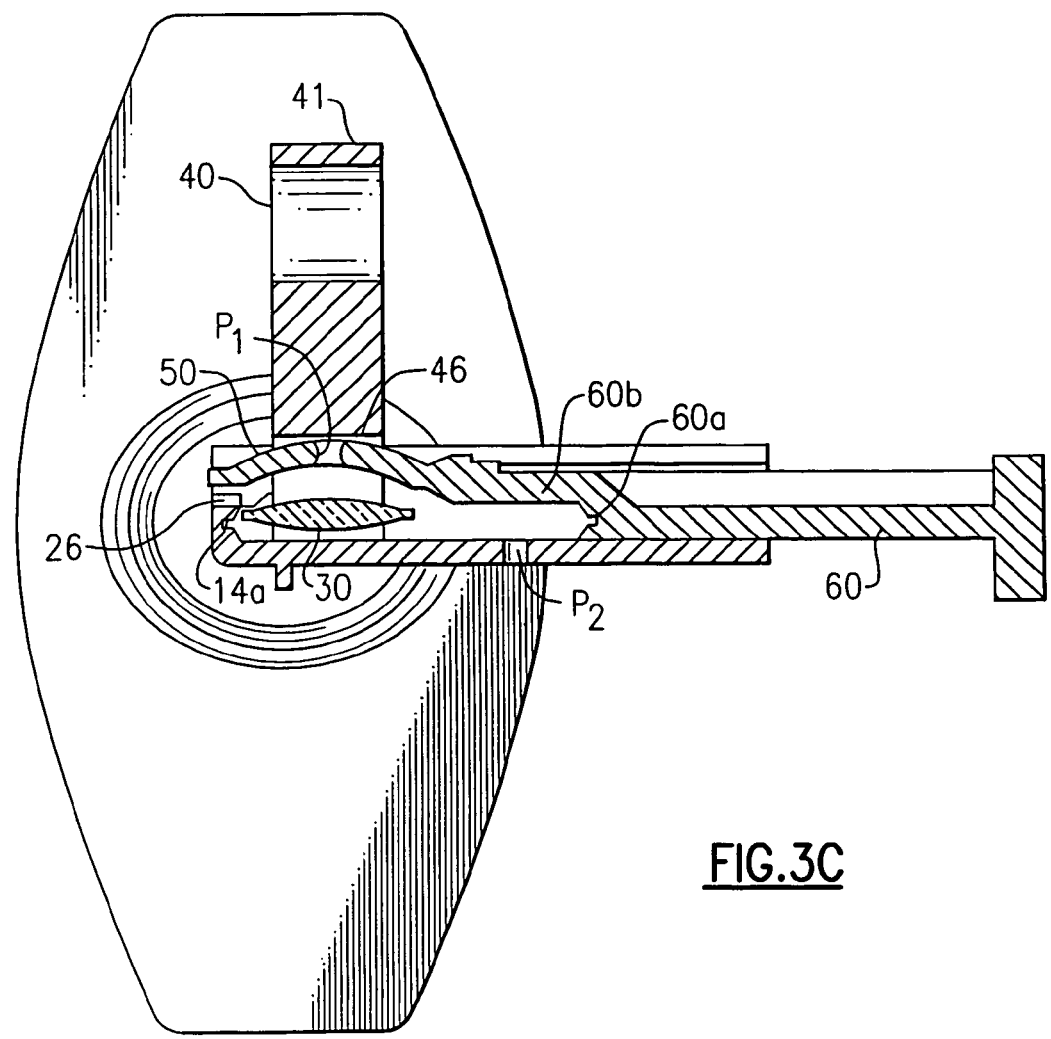
FIG. 3C is a cross-sectional view taken along the line 3C-3C of FIG. 3A.
Figure 3D:
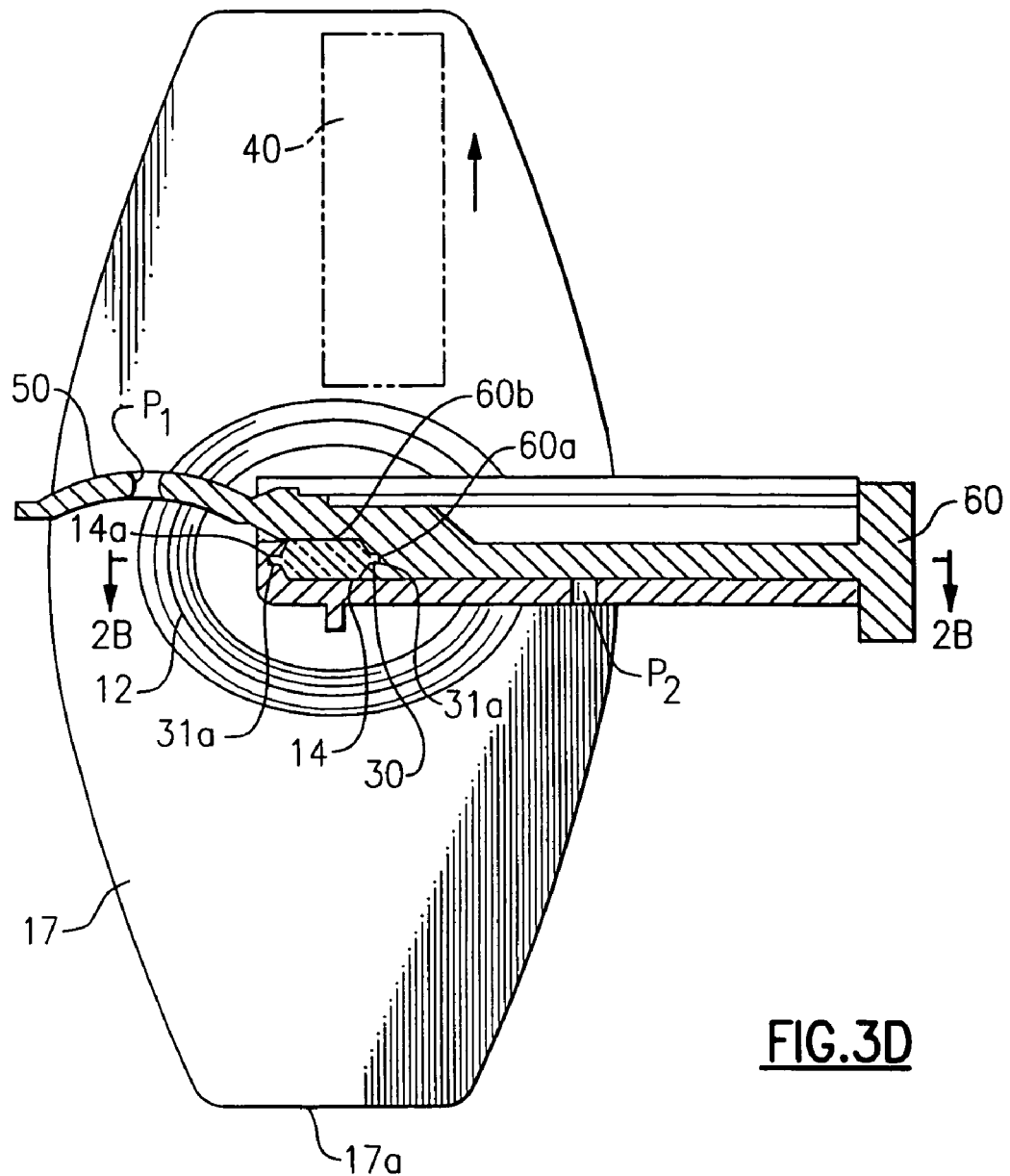
FIG. 3D is the view of FIG. 3C with the compressor drawer shown in the fully closed position.
Figure 3E:
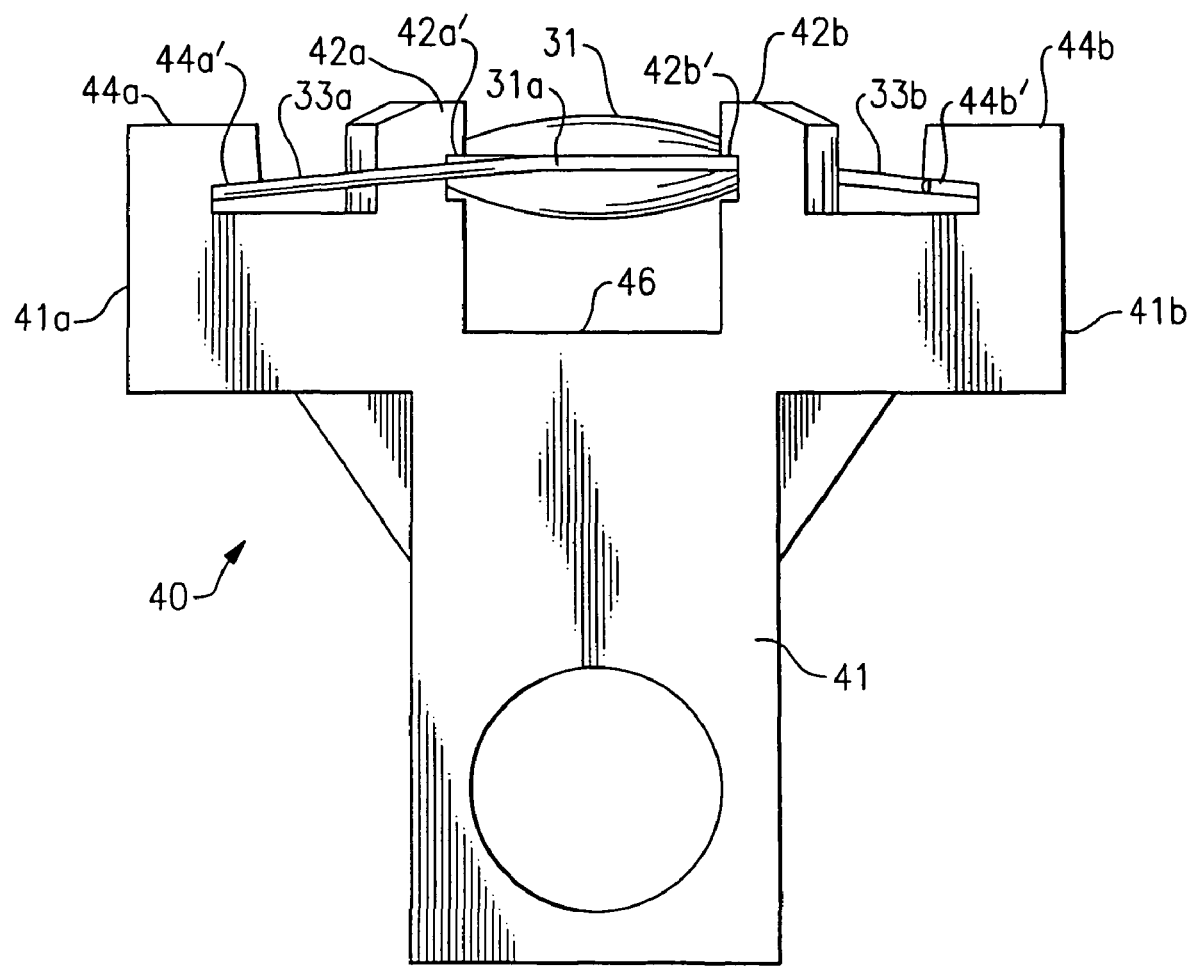
FIG. 3E is a side elevational view of the retainer and IOL coupled together.

As seen best in FIG. 3E, IOL retainer 40 includes one or more, but preferably two optic support elements 42a and 42b each having a groove 42a', 42b' or other feature for releasably supporting the IOL optic 31 at the periphery 31a thereof. Alternatively or in addition to the optic support elements, one or more, but preferably two haptic support elements 44a and 44b are provided on retainer 40, each of which include a finger 44a', 44b' or other feature for releasably supporting one or more, but preferably two haptics 33a and 33b which attach to and extend from the optic 31. In this regard, it is understood that the IOL configuration shown and described herein is for discussion purposes only, and that the present invention is not to be limited thereby. The invention may be easily adapted to IOLs of any configuration and type (e.g., IOLs with plate, open or closed loop haptics, anterior chamber IOLs, posterior chamber IOLs, accommodating IOLs (including single and double lens types), etc.). The overall configuration of the IOL retainer 40 may thus likewise vary so as to be cooperatively configured with and releasably hold the particular IOL configuration being used with the device.

The IOL retainer 40, with IOL 30 releasably held thereby, is removably attached to the injector body 12 at IOL loading bay 26 as seen in FIG. 3A. This may be done via suitable mechanical holding features which will removably connect the retainer 40 to the injector body 12, examples including friction fit, snap fit, interference fit, cooperative tabs and catches, detents, etc. As seen in FIG. 3A, retainer 40 is held in place at opening 26 via a friction fit between the surfaces defining opening 26 and the opposite outer wall surfaces 41a and 41b of retainer 40. It will be seen that when retainer 40 and IOL 30 are coupled together and attached to injector body 12, IOL optic 31 is unstressed and furthermore does not touch any part of the injector body 12.

When retainer 40 and IOL 30 are coupled together and attached to injector body 12, a stripper finger 50 is then moved between the IOL optic 31 and the center wall surface 46 of retainer 40 as seen best in FIGS. 3A and 3C. The primary function of the stripper finger 50 is to prevent the IOL 30 from lifting with the retainer 40 when the retainer is detached from the injector body (this operation will be described below). In a preferred embodiment of the invention, the stripper finger 50 is attached to the compressor drawer 60 which is movable with respect to injector body 12 between a fully open position as seen in FIG. 3B, a mid-way position seen in FIG. 3C, and the fully closed position seen in FIG. 3D. The stripper finger 50 is located between the IOL optic 31 and center wall surface 46 when the compressor 60 is in the mid-way position. When the compressor drawer 60 is moved to the fully closed position, the stripper finger 50 moves therewith and comes to rest in a position laterally adjacent the injector body 12 as seen in FIG. 3D.

Figure 2A:
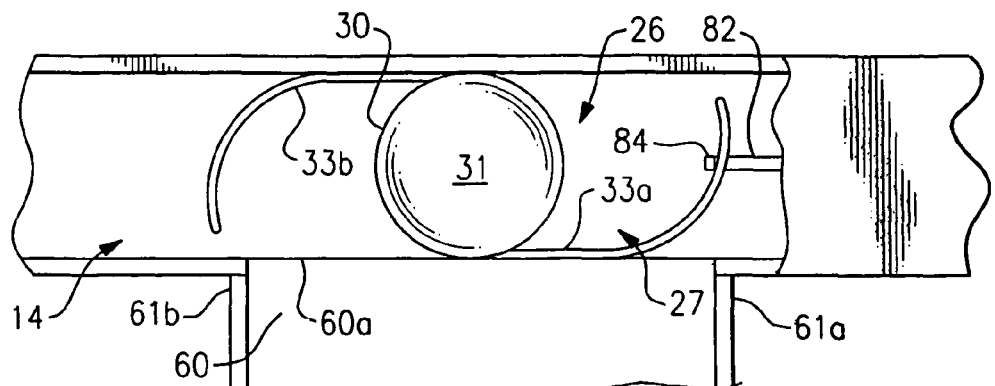
FIG. 2A is an enlarged, plan view of the loading bay portion of the injector of FIG. 1 showing an IOL positioned therein ready for compression.
Figure 2B:
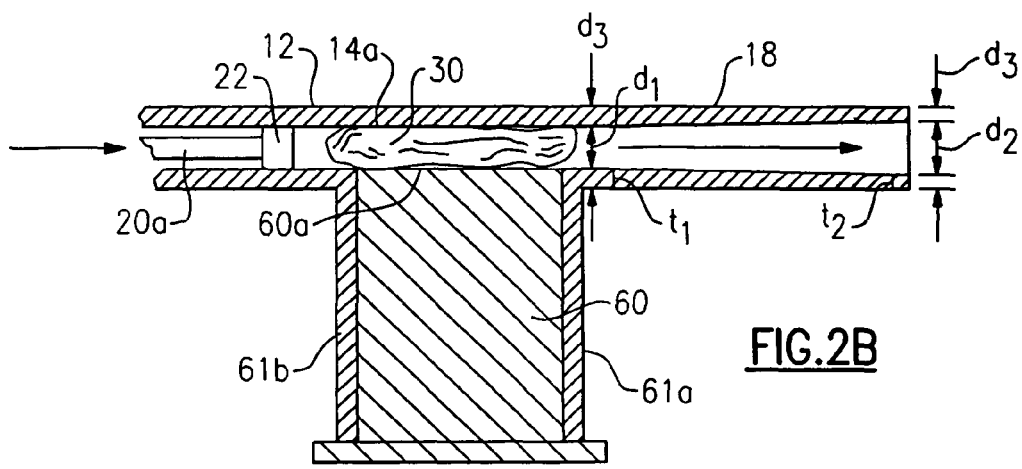
FIG. 2B is an enlarged, cross-section view taken generally along the line 2B-2B of FIG. 1 and showing an IOL compressed therein.

Referring to FIGS. 1 and 2B, it is seen that the plunger 20 includes distal and proximal plunger shaft lengths 20a, 20b, respectively, having a plunger tip 22 at the distal end thereof and a thumb press 24 at the proximal end thereof for manually operating the injector device. The plunger tip 22 is configured for engaging the IOL optic 31 at the periphery 31a thereof as the plunger 20 is advanced toward the distal tip 18a of the injector body 12. It is very important that the plunger tip 22 not damage the IOL optic 31. The plunger tip 22 is thus designed to prevent damage to the IOL optic 31. In one embodiment, the plunger tip 22 may be configured with the same cross-sectional shape and slightly smaller diameter as the lumen 14 along the length where the IOL 30 travels (i.e., from the IOL loading bay 26 to the distal tip 18a). As such, there is a close, sliding fit between the plunger tip 22 and lumen 14 and the chance of the IOL becoming wedged between these two surfaces is reduced significantly. In this embodiment of plunger 20, the inside diameter of lumen 14 may either remain constant from loading bay 26 to distal tip 18a, or increase in diameter as in the embodiment of FIGS. 2B and 2D to be described below. It is understood that other plunger tip designs may be used with the present invention as desired. It is furthermore preferred that the plunger shaft is rotationally fixed within lumen 14 to prevent unexpected rotation of the shaft (and thus the tip 22) with the lumen 14. The plunger shaft may be rotationally fixed by forming the proximal shaft length 20b and lumen 14 non-circular in cross-section or by including rotational fixing elements on the lumen inner wall and plunger shaft (e.g., longitudinal flange on the plunger having a sliding fit within a longitudinally extending groove provided on the lumen inner wall).

In a particularly advantageous embodiment, the proximal length 20b of the plunger shaft is provided with one or more elongated fingers 23a, 23b forming springs which are biased radially outwardly against the interior wall of lumen 14 (see FIGS. 1 and 6). The purpose of spring fingers 23a, 23b is to provide proper centering of the plunger shaft and tip, as well as tactile resistance between the plunger 20 and the lumen 14 as the plunger 20 is advanced therethrough. In the storage position, the plunger 20 is retracted to the position shown in FIG. 1. To ensure the plunger is not unintentionally dislodged from the injector body or unintentionally advanced within lumen 14, the spring free ends are located within respective openings 21a, 21b (opening 21b not shown) formed in the injector body 12 adjacent the proximal end 16 thereof. When it is time to use the device, the surgeon presses upon the thumb press 24 whereupon the free ends, assisted by their slanting edge faces, disengage from respective openings 21a, 21b, allowing the plunger to be freely advanced in a controlled manner through lumen 14. The bias of the spring fingers 23a, 23b against the interior wall of the lumen 14 provides the surgeon with continuous tactile feedback allowing the surgeon to advance the plunger (and thus the IOL) through the lumen 14 in a very concise and controlled manner. This feature is described more fully in our copending application Ser. No. 10/744,981.

Referring to the leading haptic 33a, it is important that the leading haptic not become "bunched up" inside the injector tip 18 as the IOL 30 is being pushed therethrough. One way to prevent this from happening is to straighten the leading haptic 33a within tip 18. To accomplish this, a haptic puller 80 is provided which is the subject of commonly assigned U.S. Pat. No. 6,491,697, the entire disclosure of which is hereby incorporated by reference. Haptic puller 80 has a shaft 82, tip 84 and finger pull 86. At assembly, the tip 84 is inserted into the injector tip with the finger pull 86 located outwardly adjacent thereto (see FIG. 4). The tip 84 is configured with a groove to engage the leading haptic 33a (see FIG. 2A). At the time of use of device 10, the haptic puller 80 is grasped at finger pull 86 and pulled away from the injector body 12, thereby engaging and straightening the leading haptic 33a within tip 18, whereupon the haptic puller 80 may be discarded.

To ensure the leading haptic 33a becomes engaged with the haptic puller tip 84 when the IOL retainer 40 is removed from injector body 12, the haptic puller tip 84 is positioned in injector tip 18 in alignment with the leading haptic 33a as it is held by the haptic supporting element 44a of IOL retainer 40. Thus, upon detaching IOL retainer 40 from the injector body 12, the leading haptic 33a releases from the haptic supporting element 44a and falls into place on the haptic puller tip 84 as shown in FIG. 2A.

To load the IOL into the delivery position seen in FIG. 2A, the nurse or surgeon grasps and removes IOL retainer 40 from injector body 12. This is accomplished by manually grasping finger grip 41 and pulling the retainer 40 away from the injector body 12 as shown by directional arrow in FIG. 3D. As described above, the stripper finger 50 acts to prevent the IOL 30 from lifting together with retainer 40. Thus, the IOL optic 31 will release from the IOL optic support element 42a, 42b and the leading and trailing haptics 33a, 33b will release from their respective haptic support elements 44a, 44b. Once the retainer 40 has been fully detached from injector body 12, it may be discarded or recycled. With the IOL 30 thus fully released from retainer 40, the IOL optic 31 comes to rest in the loading bay area 27 of the injector lumen 14 with the leading haptic 33a engaging the haptic puller tip 84 as described above. In this regard, it is noted that upon release of the IOL 30 from the retainer 40, IOL 30 will drop slightly in lumen 14. This is seen best in FIGS. 3C and 3D where in FIG. 3C, IOL 30 is held by retainer 40 with the optic periphery 31a located slightly above groove 14a which is formed in and extends longitudinally along the inside wall of lumen 14. Upon removal of retainer 40 and release of IOL 30 therefrom, the optic periphery 31a becomes aligned with groove 14a along one side of the lumen. Then, upon moving compressor drawer 60 to the fully closed position seen in FIG. 3D, the opposite edge of the optic periphery 31a becomes engaged in groove 60a of drawer 60. Thus, lumen 14 together with lumen groove 14a, drawer groove 60a, and drawer top wall 60b compresses and encases IOL optic 31 within lumen 14. The locating of the optic periphery 31a inside opposite grooves 14a and 60a ensures a planar delivery of the IOL 30 through lumen 14 and out tip 18. This manner of IOL planar delivery is described in more detail in commonly assigned U.S. Pat. No. 6,491,697 referred to above.

Figure 2C:
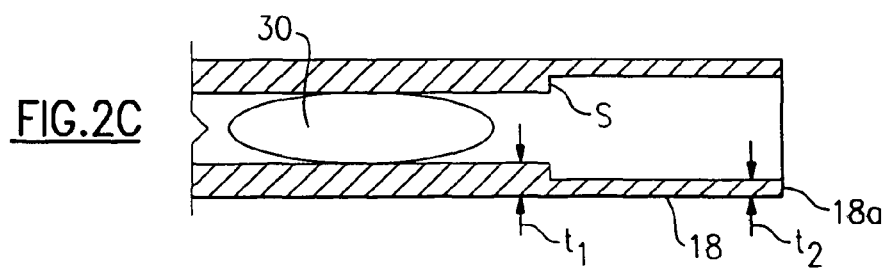
FIG. 2C is a fragmented view in cross-section of an alternate embodiment of the device tip showing a stepped increase in the inner diameter of the lumen.

As seen best in FIG. 2B, in one embodiment of the invention, the inner diameter of lumen 14 increases between IOL loading bay 26 and open distal tip 18*a* while the outer diameter remains substantially constant. Thus, at a location adjacent loading bay 26, the inner diameter $d_1$ is less than the inner diameter $d_2$ adjacent open tip 18*a* while the outer diameter $d_3$ of distal tip 18 remains substantially constant between these two points. This design is opposite to many prior art inserters which have a decreasing diameter toward the distal tip. In the prior art, the decreasing diameter is used to further compress the IOL so that the tip can fit through a very small incision in the eye (e.g., sub 3 mm). The inventors herein found that by decreasing the tip diameter as in prior art designs, greater force is needed to push the IOL through and out the device which often causes damage to the delicate IOL and/or undesired lens orientation/rotation. Thus, rather than decreasing the diameter to compress the IOL, the device body 12 herein includes an IOL loading chamber 26 and compressor drawer 60 which together compress the IOL to a desired compression size which is slightly smaller than the compression size when it exits tip 18*a*. The outer diameter $d_3$ of distal tip 18 is set to the desired incision size (e.g., sub 3 mm) and remains substantially constant from loading bay 26 to open tip 18*a*. With the inner lumen diameter increasing from the loading bay 26 to the open tip 18*a*, the compressed IOL will be urged in the distal direction (toward open tip 18*a*) since it will naturally seek a position of least compressive stress. Thus, once the plunger 20 starts advancing IOL 30 toward distal tip 18, the IOL 30 is also "pulled" in the same distal direction by the increasing diameter of the inner wall of lumen 14. This reduces the amount of force required to be applied by the plunger 20 against IOL 30 to expel it from device 10, and thereby reduces the chance of IOL damage caused by excessive plunger force. It is noted that the increasing diameter of the inner wall of lumen 14 at tip 18 may be gradual as shown in FIG. 2B, or it may be stepped at one or more junctions "S" seen in FIG. 2C as desired.

Figure 2D:
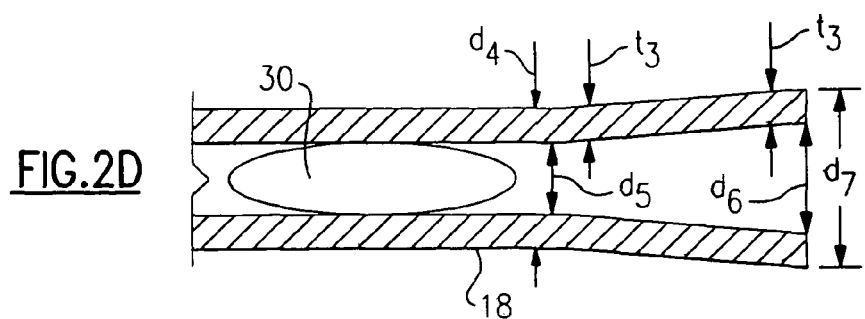
FIG. 2D is the same cross-sectional view as FIG. 2B but showing an alternate embodiment of the IOL injector.

Attention is also turned to FIG. 2D which shows another embodiment of the invention. In the embodiment of FIG. 2B described above, the inside diameter of the lumen increases while the outer diameter remains substantially constant. This is accomplished by thinning the wall of the tip 18 where the thickness $t_1$ adjacent loading bay 26 is greater than the thickness $t_2$ adjacent open tip 18*a*. In the embodiment of FIG. 2D, the thickness of the tip wall $t_3$ remains substantially constant from loading bay 26 to open tip 18*a* while the inner diameters $d_5$ and $d_6$ and outer diameters $d_4$ to $d_7$ increase from loading bay 26 to open tip 18*a*. This is accomplished by a radial tapering out of the tip adjacent open tip 18*a*. In this embodiment, it is still desirable to maintain a small diameter at open tip 18*a* (e.g., sub 3 mm) where the tip is inserted into the incision in the eye and the IOL exits the device. This requires that the outer diameter $d_4$ and inner diameter $d_5$ adjacent loading bay 26 be smaller than the corresponding outer and inner diameters $d_3$ and $d_1$ of the FIG. 2B embodiment, respectively. Thus, in the embodiment of FIG. 2D, the IOL optic 31 will be initially compressed by compressor 60 to a greater degree than in the embodiment of FIG. 2B. It is also noted that in both embodiments 2B and 2D, the length of tip 18 may be made shorter than in prior art embodiment requiring a long transition zone for successively compressing the IOL toward the open tip. This is because in the embodiments of FIGS. 2B and 2D, the IOL is subjected to successively decreasing forces as it travels toward the open tip 18*a* (rather than increasing forces imparted by the prior art devices described above), and is thus capable of a quick travel through and out the device without damage.

Prior to removing retainer 40, closing drawer 60 and compressing the IOL 30 inside the injector body, it may be desirable to apply viscoelastic to the area surrounding the IOL 30 to ease delivery of the IOL through the injector body. This is a common practice in the industry and the amount and location of viscoelastic application varies according to the instructions for use provided with the device as well as the desires of the surgeon. In any event, in a preferred embodiment, one or more viscoelastic access ports are provided on the injector device to facilitate application of the viscoelastic in the area of the IOL. One or more access ports $P_1$ may thus be provided in the form of a through-hole in stripper finger 50. The access port $P_1$ is accessible via an injection nozzle inserted into visco port $P_1$. Port $P_1$ also acts to stabilize optic 31 as it is being stripped from retainer 40 as described more fully in copending application Ser. No. 10/813,862. Alternatively or in addition to access ports $P_1$, one or more access ports $P_2$ may be provided at any desired location through the wall of tip 18 (see FIGS. 3B-D). Alternatively or in addition to visco ports $P_1$ and $P_2$, visco may be applied in loading bay 26 at the openings $P_3$ and $P_4$ defined between the optic and haptic support elements of retainer 40 (see FIG. 3A). Once the viscoelastic has been applied as desired, retainer 40 is removed and the compressor drawer 60 is moved to the fully closed position whereupon the IOL optic 31 is compressed and ready for delivery through a small incision formed in an eye. The fully closed position of compressor drawer 60 and compressed position of the IOL 30 is seen in FIG. 3D as described above. Compressor drawer 60 is slidably received between cooperatively formed drawer slides 61*a*, 61*b* extending laterally from injector body 12 adjacent opening 26. Detents or other features (not shown) may be provided on the facing surfaces of drawer slides 61*a*, 61*b* and compressor drawer 60 to assist in maintaining drawer 60 in the fully open and mid-way positions, respectively. Such drawer holding features are especially useful in preventing unintentional sliding and/or complete closing of compressor drawer 60 prior to the time needed (e.g., during storage or opening of device 10 from its associated packaging).

At this time, the haptic puller 80 is pulled away from the injector body 12 and the leading haptic 33*a* is straightened within injector tip 18. If desired or required, the plunger 20 may be advanced slightly prior to removing the haptic puller 80. The surgeon inserts the injector tip 18*a* into the incision cut into the eye and begins advancing the plunger 20. As the plunger 20 is advanced, the plunger tip 22 engages the optic periphery 31*a* and pushes IOL 30 distally. Upon continued advancement of the plunger 20, the IOL 30 is pushed through the injector tip 18*a* and is finally expressed therefrom and into the eye (FIG. 7).

What is claimed is:

1. A device for injecting a foldable IOL into an eye, said device comprising:
    an injector body including
        (a) a lumen sized to permit the IOL to be transported therethrough, the lumen having a proximal end, and an open tip wherethrough the IOL is expressed from said device, the injector body having a longitudinal axis extending between the proximal end the open tip,
        (b) a loading bay disposed in the lumen, and
        (c) an opening in said injector body, said opening being sized and shaped to receive the IOL and said opening configured and arranged to permit placement of the IOL in the loading bay, an inner diameter of the lumen at a location immediately adjacent and distal to the loading bay being less than an inner diameter of the lumen at the open tip a moveable compressor connected to the injector body proximate said opening configured and arranged to compress the IOL, the compressor movable in a direction across the longitudinal axis;

a plunger having a shaft and a plunger tip configured to slide within said lumen, the plunger movable along the longitudinal axis, said plunger configured for engaging and pushing said IOL with the plunger tip, through said lumen and out said open tip.

2. The device of claim 1, wherein the compressor comprises a compressor drawer having a leading edge, said compressor drawer being attached to said device adjacent said opening and movable to a closed position whereupon said leading edge engages and compresses said IOL.

3. The device of claim 1 wherein said injector body has an outer diameter which is substantially constant from a point adjacent said IOL when initially placed in said device to said open tip.

4. The device of claim 1 wherein said injector body has an outer diameter which increases along with the increase in diameter of said lumen.

5. The device of claim 1 wherein said lumen comprises a region of increasing diameter, and wherein said region increases gradually in diameter.

6. The device of claim 1 wherein said lumen comprises a region of increasing diameter, and wherein said region includes a step in diameter.

7. The device of claim 3 wherein said lumen comprises a region of increasing diameter, and wherein said region increases gradually in diameter.

8. The device of claim 3 wherein said lumen comprises a region of increasing diameter, and wherein said region includes a step in diameter.

9. The device of claim 4 wherein said lumen comprises a region of increasing diameter, and wherein said region increases gradually in diameter.

10. The device of claim 4 wherein said lumen comprises a region of increasing diameter, and wherein said region includes a step in diameter.

11. The device of claim 2, wherein the compressor drawer is slidable relative to the injector body and adapted such that the leading edge translates to engage and compress said IOL.

12. A device for injecting a foldable IOL into an eye, said device comprising:
   I.) an injector body including
      (a) a lumen sized to permit the IOL to be transported therethrough, the lumen having a proximal end, and an open tip wherethrough the IOL is expressed from said device, the injector body having a longitudinal axis extending between the proximal end the open tip,
      (b) a loading bay,
      (c) an opening in said injector body, said opening being sized and shaped to receive the IOL into the loading bay of the lumen,
   II.) a moveable compressor connected to the injector body proximate said opening and configured and arranged to compress the IOL when the IOL is disposed in the loading bay, the compressor movable in a direction across the longitudinal axis
   said lumen having a first diameter at a first location immediately adjacent and distal to the distal end of the loading bay and having a second diameter at the open tip that is larger than the first diameter
   III.) a plunger having a shaft and a plunger tip configured to slide within said lumen, the plunger movable along the longitudinal axis, said plunger configured for engaging with the plunger tip and pushing said IOL through said lumen and out said open tip.

13. The device of claim 12, wherein the compressor is a compressor drawer.

* * * * *